United States Patent [19]

Okamoto et al.

[11] Patent Number: 4,999,201
[45] Date of Patent: Mar. 12, 1991

[54] METHOD FOR CONTROLLING COCKROACHES

[75] Inventors: Kiku Okamoto, Toyoake; Shigeo Oki, 404 Negishi-haitsu, No. 1, 20-4 Negishi 5-chome, Urawa-shi, both of Japan

[73] Assignee: Shigeo Oki, Urawa, Japan

[21] Appl. No.: 423,031

[22] Filed: Oct. 18, 1989

Related U.S. Application Data

[63] Continuation-in-part of Ser. No. 364,507, Jun. 9, 1989, abandoned, which is a continuation of Ser. No. 203,599, Jun. 6, 1988, abandoned, which is a continuation of Ser. No. 896,144, Aug. 13, 1986, abandoned.

[30] Foreign Application Priority Data

Mar. 14, 1986 [JP] Japan .................................. 61-57963

[51] Int. Cl.$^5$ ............................................. A01N 39/00
[52] U.S. Cl. ...................................... 424/613; 514/919
[58] Field of Search ......................... 424/613; 514/919

[56] References Cited

PUBLICATIONS

Chemical Abst., 95:58582m, (1981) Okamoto.

Primary Examiner—Stanley J. Friedman
Assistant Examiner—Zohreh A. Fay
Attorney, Agent, or Firm—Wenderoth, Lind & Ponack

[57] ABSTRACT

Cockroaches can be effectively eliminated or expelled by introducing ozone into a closed space where the cockroaches are expected to inhabit so as to expose an roach-aggregation pheromone contained in cockroach feces to the ozone at a sufficient concentration, to thereby denature the aggregation pheromone to a roach-repellent substance.

7 Claims, No Drawings

METHOD FOR CONTROLLING COCKROACHES

CROSS-REFERENCE TO RELATED APPLICATIONS

This is a continuation-in-part of our copending application Ser. No. 07/364,507 filed June 9, 1989 now abandoned, which is a continuation of application Ser. No. 07/203,599 filed June 6, 1988 now abandoned, which is a continuation of application Ser. No. 06/896,144 filed Aug. 13, 1986 now abandoned.

BACKGROUND OF THE INVENTION (a) Field of the Invention

This invention relates to a method for effectively controlling cockroaches by use of an atmosphere of ozone, and more particularly to a method for denaturing a roach-aggregation pheromone contained in roach-feces to a roach-repellent substance by introducing ozone into a habitat where the roach-feces lie scattered, to thereby repel cockroaches from a human habitat.

(b) Description of the Prior Art

Hitherto there have been generally known methods for getting rid of cockroaches, which typically adopt: (1) poisonous baits, (2) slow-release chemical sprays or coatings, (3) contact poison chemicals, (4) fumigants and (5) mechanical traps. The methods using chemicals can be hazardous to man and pet animals and the effect of treatment decreases as resistance develops in the cockroaches. Mechanical trapping, i.e. the use of traps, is not efficient.

Cockroaches are known to excrete an aggregation pheromone along with their feces. The roach-aggregation pheromone is the secretion of the rectum of the cockroach and acts as an attractant, especially for larvae or nymphs. Cockroaches have the habit of hiding away in nooks and corners during daytime and crawling about in the night hours. During daytime the cockroaches are enticed by the aggregation pheromone so that they gather in dark places or other hiding places in a kitchen and so on, forming stable populations. It is known that the growth rate of cockroaches is accelerated when such populations are formed as compared with when they live independently.

One of the inventors of this invention has found and formerly reported that the attractant effect necessary for the cockroaches to live in a group, which is brought about by the aggregation pheromone contained in the roach-feces, can be deactivated by exposing the aggregation pheromone to ultraviolet rays or ozone. (Eisei-Dobutsu; Vol. 32, No. 1, pp.29–36, 1981).

The effect of deactivating the aggregation pheromone in the roach-feces as noted above is the side discovery in the experiment which was conducted by the inventors to prove that the cockroaches can be killed by being directly exposed to ultraviolet rays or ozone. To be specific, it has been found that the roach-aggregation pheromone is deactivated by coming in contact with ozone having a concentration of the order of 0.2 ppm, consequently to counteract the attractant effect of the roach-aggregation pheromone. Such deactivation of the roach-aggregation pheromone would be caused by strong oxidative effect of ozone. However, it was merely revealed that the attractant effect is counteracted due to the deactivation of the roach-aggregation pheromone by use of ozone. In other words, only the fact that ozone can denature the roach-feces to a substance having no effect on the cockroaches was presented. That is to say, the use of ozone was by no means envisaged for the purpose of exterminating or repelling the cockroaches.

In the stage of having issued the report on the deactivation of the roach-aggregation pheromone as mentioned above, it has been hitherto inconceivable that the cockroaches can be repelled by exposing the roach-feces to ultraviolet rays or ozone, like the method of killing the cockroaches by use of ultraviolet rays or ozone is not deemed practical in general. To be more specific, the idea of denaturing the roach-feces to a roach-repellent substance capable of getting rid of cockroaches has not been proposed, much less has there been proposed a method of obtaining such a roach-repellent substance by use of ozone.

OBJECT OF THE INVENTION

An object of this invention is to provide a method for readily denaturing an aggregation pheromone contained in the feces of cockroaches to a roach-repellent substance capable of effectively getting rid of the cockroaches without remaining a deleterious substance harmful to man and beast in human living environment after treatment.

SUMMARY OF THE INVENTION

To attain the object described above according to this invention, there is provided a method for controlling cockroaches, which comprises exposing cockroach feces to ozone at a concentration of 0.5 ppm to 20 ppm, and continuing the exposure to ozone for the time determined in accordance with the concentration of ozone so as to denature an aggregation pheromone contained in the cockroach feces to a roach-repellent substance.

Upon airtightly closing off a space where the roach-feces lie scattered, such as a roach-ridden kitchen, ozone is introduced into the closed space. The introduction of ozone is carried out by continuously operating at least one ultraviolet lamp or ozonizer disposed in the closed space. Though the time for exposure to ozone depends on the concentration of ozone in the closed space, the ozone-exposing treatment for several ten minutes to about 8 hours gives rise to a striking effect of denaturing the aggregation pheromone contained in the roach-feces to a roach-repellent substance. The ozone-exposing treatment causes cockroaches present in the closed space during treatment to die and brings about the repelling effect so as to forbid outside cockroaches to enter the treated space for a long time.

By applying ultrasonic vibration to the cockroach feces being exposed to ozone, deactivating of the roach-aggregation pheromone can be promoted increasingly.

The above and further objects and features of the invention will more fully appear from the following detailed description.

DESCRIPTION OF THE PREFERRED EMBODIMENT

The method for controlling cockroaches according to this invention can be practiced by exposing feces excreted by the cockroaches to an atmosphere of relatively high-concentrated ozone. An aggregation pheromone contained in the roach-feces is denatured to a roach-repellent substance by the ozone so as to keep the roaches at a distance. The ozone to which the roach-feces are exposed should be at considerably high concentration in the range of 0.5 ppm to 20 ppm. For instance, by exposing the roach-feces to the ozone having a concentration of 0.5 ppm for about 8 hours, the aggregation pheromone contained in the roach-feces, which has an attractant effect on the cockroaches, is not only completely deactivated but also denatured to the roach-repellent substance. Though the effect of deactivating the aggregation pheromone is heightened with an increase in ozone concentration, it is preferable to determine the ozone concentration below 20 ppm for safety so that men and beasts are protected from being badly affected by intense ozone at the worst. It has been confirmed that the roach-aggregation pheromone is denatured to the roach-repellent substance by being exposed to ozone having the maximum concentration of 20 ppm for several ten minutes.

The time for exposure to ozone as specified above depends on the environmental conditions such as environmental temperature, concentration of oxygen and the state of the aggregation pheromone contained in the roach-feces. As will be described later in detail, it has been known that a pure aggregation pheromone extracted experimentally from the roach-feces is readily denatured in an extremely short time by exposure to ozone. From the viewpoint of practical use, it is desirable to determine the time for exposure to ozone as short as possible.

The processes for practicing the method for controlling cockroaches according to this invention will be described.

At the outset, the space where cockroaches are expected to inhabit is closed off so as to be made substantially airtight. The habitat of the cockroach can be distinguished by the roach-feces scattered there. When the habitat is closed airtightly in practice, the whole space of, for example, a kitchen should be shut and, as occasion arises, doors and windows may be sealed up. Into the roach habitat thus closed, highly concentrated ozone as touched upon above is introduced from the outside. Otherwise, the ozone may be generated in the closed habitat by operating one or more ozone generators previously disposed in the habitat. As the ozone generator, there may be used an ultraviolet lamp or ozonizers of various types.

After the prescribed time for exposure to ozone proceeds, the closed habitat is opened and ventilated sufficiently. Thus, the treatment of exposing the aggregation pheromone contained in the roach-feces to ozone is finished. The ozone is spontaneously changed to oxygen with time. In general, 30 minutes after ceasing the generation of ozone, the ozone completely turns to oxygen. Therefore, ventilation of the habitat is not necessarily carried out.

The introduction of the highly concentrated ozone into the closed habitat of cockroaches brings about an advantageous roach-repelling effect, not to mention, causes the cockroaches confined therein to die. That is, the aggregation pheromone contained in the roach-feces scattered in the closed habitat, which originally has an effect of enticing the cockroaches, is denatured to a repellent substance hated by the cockroaches to thereby forbid the cockroaches to enter the space thus treated. The roach-repelling effect obtained by exposing the roach-feces to the ozone having a concentration of about 10 ppm for about 4 hours was maintained for about one week. When lessening the roach-repelling effect, the habitat of the cockroaches may be again exposed to ozone in the same manner as mentioned above.

The method according to this invention can produce a marked effect of repelling cockroaches and be practiced at a low cost. Besides, the method of this invention is safe because no poisonous substance is used. Furthermore, intense bactericidal action of ozone can not only keep fixtures and household articles in the space to be treated from getting moldy, but also prevent the propagation of bacteria and produce sterilizing action to preserve foods from decay.

Though this invention places no specific restriction on the type of the ozone generator, it is preferable for practicing the method of this invention to use an ozone generator of the type utilizing corona discharge which is generally called "a silent electric discharge" or an ultraviolet lamp which operates quietly. On the other hand, an arc-discharge ozonizer utilizing arc discharge (spark discharge) between dielectric electrodes may be applied for the present method, though it produces a destructive sound when operated to produce ozone.

Before going into an explanation of the actual proof of the marked effect of repelling cockroaches brought about by this invention, it will be appropriate at this point to clarify the fact that the aggregation pheromone of the cockroaches can be deactivated by exposure to ozone on reference to the following experimental results.

At first, the method through which the experiments for elucidating the effect of this invention were conducted will be explained below.

The aggregation pheromone extracted from the feces of *Periplaneta Americana* by use of methanol and the non-treated roach-feces containing the aggregation pheromone were used as test materials. The ozone concentration and exposure time were varied in steps and the changes in pheromone activity were investigated by bioassay as noted below.

Two kinds of filter papers (2 cm $\times$ 10 cm), which were predicted to differ in aggregation pheromone activity, were respectively folded into the shape of the letter W and set in the erect position within a dish (10 cm diameter and 2.5 cm deep). About larvae of cockroaches were placed in the dish, which was allowed to stand for 1 hour for a preference test. After the above 1-hour period, the number of larvae attracted to each filter paper was counted to determine the relative aggregation pheromone activity of the two filter papers.

The aggregation pheromone-active filter papers used in the experiments were as follows: One of them was a filter paper on which feces of cockroaches were deposited (hereinafter referred to as feces-deposited filter paper) and the other was prepared by extracting the aggregation pheromone from the feces of cockroaches and immersing a filter paper in the resulting aggregation pheromone-containing extract (hereinafter referred to as extract-imbibed filter paper). To prepare the feces-deposited filter paper, a filter paper was allowed to stand in a multiple feeder for Periplaneta Americana so as to have their feces spontaneously deposited on the filter paper. The rectangular portion of filter paper showing a uniform deposit of feces (2 cm $\times$ 10 cm) was cut out and used in the experimentation.

To prepare the extract-imbibed filter paper, feces collected from the multiple feeder was mixed with 3 volumes of methanol and, after overnight standing, the mixture was filtered though a single web of gauze. Strips of filter paper sized 2 cm $\times$ 10 cm were then immersed in the filtrate, 20 strips per 100 of methanol, and finally dried in the air.

The feces-deposited filter paper or the extract imbibed filter paper was left standing for predetermined period of time in a container communicating with an ozone generating device. The filter paper taken out from the container was allowed to stand overnight in a room until the ozone odor was eliminated. The concentration of ozone was measured by means of a gas detection tube.

EXPERIMENT 1

[Confirmation of aggregation pheromone activity in the feces-deposited filter paper or the extract-imbibed filter paper]

Using the feces-deposited filter paper, the extract-imbibed filter paper and an untreated, plain filter paper completely free of pheromone activity (2 cm $\times$ 10 cm), the preference test described above was carried out.

EXPERIMENT 2

[Determination of the decrease in aggregation pheromone activity due to ozone treatment]

A preference test was carried out in the same manner as above using the feces-deposited filter paper, the extract-imbibed filter paper and the corresponding ozone-treated filter papers.

EXPERIMENT 3

[Confirmation of aggregation pheromone activity in the ozone-treated filter papers]

The same preference test as above was carried out using the ozone-treated filter papers and the untreated filter paper.

One hour after commencement of the preference test, one or two individuals were at times found not attracted to the filter paper but crawling around in the dish. On the assumption that all of these migrant larvae would ultimately attach themselves to either one of the filter papers, the number of individuals which are not attracted to the filter papers and crawls around in the dish was divided by two and the quotient was added to the count for each filter paper. Then, the percentages of larvae attracted to the respective filter paper were calculated.

The experiment was replicated 10 times and the mean percentage of larvae attached to each filter paper and the standard deviation were calculated and the analysis of the significant difference in mean values was examined.

The results of the Experiment 1 described above are shown in Table 1.

TABLE 1

EXPERIMENT 1:
Confirmation of pheromone activity in filter paper

| Number of larvae | Replicate | Extract-imbibed filter paper | Untreated filter paper | Level of significance |
|---|---|---|---|---|
| (a) Extract-imbibed filter paper: | | | | |
| 20.0 ± 0.0 | 10 | 92.3 ± 6.7% | 7.8 ± 6.7% | 0.001 |
| 20.0 ± 0.0 | 10 | 87.0 ± 6.8% | 13.0 ± 6.8% | 0.001 |
| (b) Feces-deposited filter paper: | | | | |
| 20.3 ± 0.6 | 10 | 95.3 ± 7.5% | 4.9 ± 7.5% | 0.001 |
| 19.8 ± 0.6 | 10 | 81.8 ± 7.0% | 18.1 ± 7.0% | 0.001 |

In every case, significantly more larvae attached themselves to the feces-deposited filter paper and the extract-imbibed filter paper, both of which were predicted to contain pheromone activity, as compared with those attached to the untreated filter paper (significant differences at the 0.001% level). It is therefore apparent that both the feces-deposited filter paper and the extract-imbibed filter paper had pheromone activity.

The results of the Experiment 2 are shown in Table 2.

If the ozone treatment caused no change in pheromone activity, there should not be a significant difference between the percentage of larvae attaching themselves to the pheromone-treated filter paper and that of larvae attached to the corresponding ozone-treated filter paper.

When the extract-imbibed filter paper was used, treating it with 0.5 ppm of ozone for at least 10 minute resulted in a change in pheromone activity. At an ozone concentration of 2.7 ppm, an exposure time of 3 minutes did not cause a significant difference in the mean percentage of larvae attached between the two filter papers but after 5 minutes of exposure more larvae were attracted to the extract-imbibed filter paper (a significant difference at the 0.001% level), suggesting a change in pheromone activity due to exposure to ozone.

When the feces-deposited filter paper was used, a 5-minute exposure to 2.7 ppm of ozone caused no significant difference in the percentage of larvae attached between the feces-deposited filter paper and the corresponding ozone treated filter paper but when the duration of exposure was 10 minute or longer, more larvae attached themselves to the feces-deposited filter paper at the 0.001% level of significance.

TABLE 2

EXPERIMENT 2: Determination of the decrease in pheromone activity due to exposure to ozone

| Time of exposure (min.) | Number of larvae | Replicate | Extract-imbibed filter paper | Untreated filter paper | Level of significance |
|---|---|---|---|---|---|
| (a) Extract-imbibed filter paper: | | | | | |
| Concentration of ozone = 0.5 ppm | | | | | |
| 10 | 20.0 ± 0.0 | 10 | 89.8 ± 11.2% | 10.3 ± 11.2% | 0.001 |
| 20 | 20.0 ± 0.0 | 10 | 61.8 ± 23.3% | 38.3 ± 23.3% | 0.05 |
| 30 | 20.0 ± 0.0 | 10 | 83.3 ± 8.7% | 16.8 ± 8.7% | 0.001 |
| 40 | 20.0 ± 0.0 | 10 | 87.8 ± 7.5% | 12.3 ± 7.5% | 0.001 |
| 50 | 20.0 ± 0.0 | 10 | 95.8 ± 10.4% | 4.3 ± 10.4% | 0.001 |
| 60 | 20.0 ± 0.0 | 10 | 86.5 ± 16.5% | 13.0 ± 16.5% | 0.001 |
| Concentration of ozone = 2.7 ppm | | | | | |
| 3 | 20.0 ± 0.0 | 10 | 51.3 ± 32.6% | 48.8 ± 32.6% | |
| 5 | 20.0 ± 0.0 | 10 | 87.5 ± 5.2% | 12.5 ± 5.2% | 0.001 |
| 7 | 20.0 ± 0.0 | 10 | 85.7 ± 15.1% | 14.3 ± 15.1% | 0.001 |
| 8 | 20.0 ± 0.0 | 10 | 89.5 ± 10.5% | 10.5 ± 10.5% | 0.001 |
| 9 | 20.0 ± 0.0 | 10 | 72.0 ± 12.7% | 28.0 ± 12.7% | 0.001 |

TABLE 2-continued

EXPERIMENT 2: Determination of the decrease in pheromone activity due to exposure to ozone

| Time of exposure (min.) | Number of larvae | Replicate | Extract-imbibed filter paper | Untreated filter paper | Level of significance |
|---|---|---|---|---|---|
| 10 | 20.0 ± 0.0 | 10 | 88.3 ± 7.7% | 13.6 ± 7.7% | 0.001 |
| (b) Feces-deposited filter paper: | | | | | |
| Concentration of ozone = 2.7 ppm | | | | | |
| 5 | 19.4 ± 1.5 | 10 | 56.1 ± 24.2% | 43.9 ± 24.2% | — |
| 10 | 20.0 ± 0.0 | 10 | 87.0 ± 13.1% | 13.0 ± 13.1% | 0.001 |
| 15 | 20.0 ± 0.0 | 10 | 98.5 ± 3.2% | 1.5 ± 3.2% | 0.001 |
| 30 | 19.1 ± 1.1 | 10 | 95.4 ± 4.6% | 4.6 ± 4.6% | 0.001 |
| 45 | 19.7 ± 0.8 | 10 | 94.2 ± 5.8% | 5.8 ± 5.8% | 0.001 |
| 60 | 19.9 ± 0.7 | 10 | 98.8 ± 2.5% | 1.2 ± 2.5% | 0.001 |
| Concentration of ozone = 13.4 ppm | | | | | |
| 8 | 19.8 ± 0.4 | 10 | 59.1 ± 10.7% | 41.0 ± 10.7% | 0.01 |
| 9 | 18.9 ± 1.5 | 10 | 55.9 ± 11.3% | 44.0 ± 11.4% | 0.05 |
| 10 | 19.9 ± 1.5 | 10 | 93.3 ± 6.2% | 6.8 ± 6.2% | 0.001 |
| 30 | 19.4 ± 0.8 | 10 | 74.6 ± 20.1% | 28.0 ± 19.6% | 0.001 |
| 60 | 19.8 ± 0.8 | 10 | 70.5 ± 14.4% | 20.5 ± 14.3% | 0.001 |

When the ozone concentration was 13.4 ppm, the level of significance was slightly higher at 0.01% or 0.05% after 8 or 9 minutes of exposure but in other instances, more larvae gathered on the feces-deposited filter paper at the 0.001% level.

Therefore, the above experimental results indicate that the aggregation pheromone activity is reduced by ozone in a fairly short time.

The results of Experiment 3 are set forth in Table 3.

The experiment was conducted on the following premise. Thus, if ozone treatment caused a mere reduction in aggregation pheromone activity, many larvae would still be attracted to the ozone-treated filter paper, while if the pheromone was completely inactivated, there would be no difference from the non-treated filter paper.

Irrespective of which of the feces-deposited filter paper and extract-imbibed filter paper was used, many larvae were found on the ozone-treated paper after a short duration of exposure. As the exposure time was increased, more cockroaches avoided the ozone-treated paper and attached themselves to the plain filter paper. It appears, that a short time of exposure to ozone caused an increased reduction in aggregation pheromone activity but a longer exposure converted the pheromone to a repellent substance.

When the fecal pheromone extract was used, reversal of the proportions of larvae attracted between the extract-imbibed paper and the ozone-treated filter paper occurred after 30 to 50 minutes of exposure at the ozone concentration of 0.5 ppm. The corresponding time of reversal with the feces-deposited filter paper was 10 to 15 minutes

TABLE 3

EXPERIMENT 3: Confirmation of pheromone activity in filter paper

| Time of exposure (min.) | Number of larvae | Replicate | Extract-imbibed filter paper | Untreated filter paper | Level of significance |
|---|---|---|---|---|---|
| (a) Extract-imbibed filter paper: | | | | | |
| Concentration of ozone = 0.5 ppm | | | | | |
| 10 | 20.0 ± 0.0 | 10 | 57.3 ± 31.3% | 42.8 ± 31.3% | — |
| 20 | 20.0 ± 0.0 | 10 | 61.3 ± 20.8% | 38.8 ± 15.8% | 0.05 |
| 30 | 20.0 ± 0.0 | 10 | 59.5 ± 15.8% | 40.5 ± 15.8% | 0.05 |
| 40 | 20.0 ± 0.0 | 10 | 47.8 ± 20.3% | 52.3 ± 20.3% | — |
| 50 | 20.0 ± 0.0 | 10 | 15.3 ± 18.2% | 84.8 ± 18.2% | 0.001 |
| 60 | 20.0 ± 0.0 | 10 | 28.0 ± 33.2% | 72.0 ± 33.2% | 0.01 |
| Concentration of ozone = 2.7 ppm | | | | | |
| 3 | 20.0 ± 0.0 | 10 | 57.4 ± 25.1% | 42.6 ± 25.1% | — |
| 5 | 20.0 ± 0.0 | 10 | 63.3 ± 20.7% | 36.8 ± 20.8% | 0.01 |
| 7 | 20.0 ± 0.0 | 10 | 20.5 ± 15.4% | 79.5 ± 15.4% | 0.00 |
| 8 | 20.0 ± 0.0 | 10 | 31.8 ± 31.2% | 68.3 ± 31.2% | |
| 9 | 20.0 ± 0.0 | 10 | 21.5 ± 10.9% | 78.5 ± 10.8% | |
| 10 | 20.0 ± 0.0 | 10 | 25.8 ± 23.1% | 74.3 ± 23.1% | 0.00 |
| (b) Feces-deposited filter paper: | | | | | |
| Conentration of ozone = 2.7 ppm | | | | | |
| 5 | 20.0 ± 0.0 | 10 | 95.8 ± 4.5% | 4.3 ± 4.5% | 0.00 |
| 10 | 20.1 ± 0.3 | 10 | 70.8 ± 24.9% | 29.2 ± 24.9% | 0.01 |
| 15 | 19.7 ± 6.4 | 10 | 29.3 ± 18.4% | 70.7 ± 18.4% | 0.00 |
| 30 | 19.1 ± 1.3 | 10 | 29.3 ± 18.4% | 70.7 ± 18.4% | 0.00 |
| 45 | 19.9 ± 0.7 | 10 | 26.3 ± 27.0% | 73.8 ± 27.0% | 0.01 |
| 60 | 20.0 ± 0.0 | 10 | 15.5 ± 10.6% | 84.5 ± 10.6% | 0.00 |
| Concentration of ozone = 13.4 ppm | | | | | |
| 8 | 19.5 ± 0.7 | 10 | 60.9 ± 10.8% | 39.2 ± 10.8% | 0.001 |
| 9 | 18.1 ± 2.3 | 10 | 63.2 ± 13.0% | 36.8 ± 13.0% | 0.001 |
| 10 | 19.9 ± 0.3 | 10 | 39.7 ± 15.9% | 60.3 ± 15.9% | 0.01 |
| 30 | 19.7 ± 0.5 | 10 | 25.4 ± 20.1% | 77.5 ± 20.1% | 0.001 |
| 60 | 19.4 ± 0.8 | 10 | 21.2 ± 26.4% | 78.8 ± 26.4% | 0.001 | at the ozone concentration of 2.7 ppm and 9 to 10 minutes at the ozone concentration of 13.4 ppm.

The results of experiments proved that the aggregation pheromone of cockroaches is deactivated by ozone. Taking note of such an effect of deactivating the aggregation pheromone, the method of denaturing the aggregation pheromone to a roach-repellent substance has been established according to this invention and will be described below with reference to practical experiments.

EXPERIMENT 4

The experiment was carried out inside the kitchen of a restaurant (179 $m^2$ in floor area and 426 $m^3$ in volume) in such a manner that seven ozone generators each composed of an ultraviolet lamp were suspended from the ceiling of the kitchen and continuously operated to generate ozone from 10:00 p.m. to next 5:00 a.m every day. The ozone generated was below 0.6 ppm for first nine days, and thereafter, above 0.6 ppm. At 3:00 p.m. every day, the number of cockroaches caught in several adhesive traps located dispersively the kitchen was counted. The number of cockroaches caught respectively in the traps on specific locations I–III in the kitchen is shown in Table 4 below.

TABLE 4

(The number of cockroaches caught at locations I–III)

| | Concentration of ozone (ppm) | LOCATION I | II | III | Total number |
|---|---|---|---|---|---|
| 1st day | Below 0.6 | 58 | 66 | 174 | 248 |
| 2nd day | Below 0.6 | 64 | 15 | 160 | 239 |
| 3rd day | Below 0.6 | 36 | 2 | 155 | 193 |
| 4th day | Below 0.6 | 100 | 1 | 147 | 248 |
| 5th day | Untreated | | | | |
| 6th day | Below 0.6 | 141 | 103 | 176 | 420 |
| 7th day | Below 0.6 | 81 | 9 | 59 | 149 |
| 8th day | Below 0.6 | 31 | 18 | 30 | 79 |
| 9th day | Below 0.6 | 77 | 14 | 38 | 129 |
| 10th day | Above 0.6 | 56 | 8 | 44 | 108 |
| 11th day | Above 0.6 | 17 | 8 | 34 | 59 |

Just after interruption of the experimental test on the 5th day, the number of cockroaches caught in the traps was ephemerally increased to that before the test. That is, before treating the kitchen with ozone, 300 to 400 cockroaches were caught per day. However, as is evident from Table 4, the cockroaches caught in the traps were considerably decreased in number after treatment with ozone having a relatively low concentration of about 0.6 ppm. Thus, it is found that ozone produces the roach-repelling effect. Ozone treatment continuously carried out since then caused the cockroaches in the kitchen to be remarkably decreased in number after the 12th day.

EXPERIMENT 5

The experiment was carried out in a restaurant on a small scale (63 $m^2$ in floor area and 145 $m^3$ in volume) by use of two ozone generators. The ozone generators were operated for eight hours every day so as to produce an atmosphere of ozone having a relatively high concentration of about 5 ppm in the restaurant. The experiment began late in October. The results of exposure to ozone were measured by counting the number of cockroaches caught in roach traps set on five locations (I–V) in the restaurant and are shown in Table 5 below.

TABLE 5

(The number of cockroaches caught at locations I–V)

| | Location I | II | III | IV | V | Total |
|---|---|---|---|---|---|---|
| 7 months before | 74 | 83 | 132 | 90 | 95 | 474 |
| Just after | 60 | 70 | 45 | 59 | 56 | 290 |
| 3 weeks after | 45 | 57 | 46 | 50 | 28 | 226 |
| 5 weeks after | 45 | 52 | 35 | 25 | 30 | 187 |
| About 8 weeks after | 38 | 12 | 4 | 5 | 26 | 85 |

As is evident from this experiment, the cockroaches caught in the traps were considerably decreased in number after treatment with ozone having a relatively high concentration. The results of the experiment proved that the cockroaches present in their habitat were considerably decreased in number of introducing ozone. The number of cockroaches caught in the traps about 8 weeks after commencement of the experiment is about one-sixth of that just after commencement of the experiment.

As is plain from the experimental results noted above, an aggregation pheromone contained in the roach-feces can be denatured to a roach-repellent substance by introducing ozone having a concentration of 0.5 ppm to 20 ppm to a closed space where the cockroaches are expected to inhabit so as to expose roach-feces to ozone. Though the roach-feces containing the roach-aggregation pheromone thus denatured to the roach-repellent substance by exposure to ozone are utilized to get rid of cockroaches, a roach-repellent substance may be obtained by exposing an aggregation pheromone-containing extract extracted from the feces of cockroaches to ozone and finely powdered or granulated so that the powdered or granulated repellent substance can be distributed over a habitat of cockroaches.

When applying ozone to the feces of cockroaches or the aforementioned aggregation pheromone-containing extract from the feces of cockroaches to obtain the roach-repellent substance, the aggregation pheromone in the roach-feces of extract can be denatured to the roach-repellent substance with notably high efficiency by vibrating the roach-feces or extract by use of ultrasonic waves. Furthermore, the denaturing efficiency of changing the aggregation pheromone into the roach-repellent substance can be remarkably improved by operating the ozonizer to produce ozone in an atmosphere of high-concentrated oxygen. Thus, the method of improving the denaturing efficiency can produce the roach-repellent substance having a marked effect in a short time.

As is clear from the description given above, by practicing the method for controlling cockroaches according to the present invention, which comprises closing airtightly a space where cockroaches are expected to inhabit and introducing ozone into the closed space for prescribed hours, cockroaches present in the closed space during treatment can be effectively exterminated and the repelling effect can be readily brought about so as to forbid outside cockroaches to enter the treated space. Since the atmosphere of ozone is used, fixtures and household articles in the space to be treated can be kept from getting moldy due to intense bactericidal action of ozone, and besides, the propagation of bacteria can be prevented and sterilizing action can be produced to preserve foods from decay. Moreover, the method of this invention is safe because no poisonous substance is used. Thus, the method according to this invention can produce a marked effect of repelling cockroaches and be practiced at a low cost.

As can be readily appreciated, it is possible to deviate from the above embodiments of the present invention and, as will be readily understood by those skilled in this art, the invention is capable of many modifications and improvements within the scope and spirit thereof. Accordingly, it will be understood that the invention is not to be limited by these specific embodiments, but only by the scope and spirit of the appended claims.

What is claimed is:

1. A method for controlling cockroaches, which comprises substantially airtightly forming a closed space where cockroach feces lie scattered, introducing ozone into the closed space to expose the cockroach feces present in the closed space to ozone at a concentration of 0.5 ppm to 20 ppm, continuing the exposure to ozone for a period of time of about several ten minutes up to about 8 hours so as to cause the cockroaches present in the closed space during treatment to die and to denature an aggregation pheromone contained in the cockroach feces so as to form a roach-repellent substance.

2. The method according to claim 1, wherein at least one ultraviolet lamp or ozonizer is disposed in the closed space and continuously operated to produce ozone in the closed space.

3. The method according to claim 1, wherein ultrasonic vibration is applied to the cockroach feces being exposed to ozone to improve denaturing efficiency to the roach-repellent substance.

4. The method according to claim 1, wherein ozone is produced in an atmosphere of high-concentrated oxygen to improve denaturing efficiency to the roach-repellent substance.

5. A method for controlling cockroaches, which comprises extracting a roach-aggregation pheromone from the feces of cockroaches by use of methanol, exposing the extracted roach-aggregation pheromone to ozone at a concentration of 0.5 ppm to 20 ppm for several ten minutes to about 8 hours to denature said extracted roach-aggregation pheromone to form a roach-repellent substance, and powdering or granulating said roach-repellent substance to obtain repellent powder or grain capable of being distributed over a habitat of cockroaches.

6. The method according to claim 5, wherein ultrasonic vibration is applied to the cockroach feces being exposed to ozone to improve denaturing efficiency to the roach-repellent substance.

7. The method according to claim 5, wherein ozone is produced in an atmosphere of high-concentrated oxygen to improve denaturing efficiency to the roach-repellent substance.

* * * * *